United States Patent [19]

Machida et al.

[11] Patent Number: 4,935,239

[45] Date of Patent: Jun. 19, 1990

[54] COMPOSITION FOR ANTIVIRAL MEDICINES

[75] Inventors: Makoto Machida, Tokorozawa; Makoto Yashiro; Eiko Takezawa, both of Tokyo; Sachiko Nanbara, Yokohama, all of Japan

[73] Assignee: Sanyo-Kokusaku Pulp Co., Ltd., Tokyo, Japan

[21] Appl. No.: 325,975

[22] Filed: Mar. 20, 1989

[30] Foreign Application Priority Data

Apr. 12, 1988 [JP] Japan .................................. 63-88296

[51] Int. Cl.$^5$ ...................... A61K 35/78; A61K 31/70
[52] U.S. Cl. .................................... 424/195.1; 514/22
[58] Field of Search ........................ 424/195.1; 514/22

[56] References Cited

U.S. PATENT DOCUMENTS 4,185,097  1/1980  Ward et al. ...................... 424/195.1

Primary Examiner—John W. Rollins
Attorney, Agent, or Firm—Oblon, Spivak, McClelland, Maier & Neustadt

[57] ABSTRACT

A composition for anti-AIDS viral and other antiviral medicines having spent liquor from pulping and/or processed products thereof as major constituents and preventive and/or therapeutic method(s) against AIDS viral and other viral infections are presented.

7 Claims, No Drawings

COMPOSITION FOR ANTIVIRAL MEDICINES

BACKGROUND OF THE INVENTION

The present invention relates to the use of lignin derivatives for antiviral drugs, in particular, to the prevention and the therapy against AIDS (Acquired Immune Deficiency Syndrome) virus.

The number of patients with AIDS has abruptly increased in recent times, centering in U.S.A. and Africa currently it amounts to about fifty thousand persons, the virus carriers being existent in about a hundred times as many persons, all over the world. It is said that almost all virus carriers come down with disease within five years and the death rate reaches about 100%. AIDS makes the immune system of living bodies come to collapse by virtue that AIDS virus infects the helper T cells governing the immune system and destroys them. As a result, persons fall the opportunistic infection, malignant tumor or the like to die with this disease.

Up to this date, nucleic acid-based AZT (azidothymidine) alone is approved for the therapeutic drug against AIDS. The AZT, however, cannot stand the use for a long term due to the intensive side effects (anemiz etc.).

On the other hand, lignin exists abundantly in the world of nature after cellulose, is contained in almost all plants, and has been ingested by human being as a part of foods. In recent, the physiological effects (effect for intestinal disorders etc.) thereof are attracting an attention as a kind of vegetable fibers. Moreover, the lignin derivatives are produced centering the spent liquor in the pulp and paper industry. The potential thereof as a medicinal drug is, however, hardly investigated and merely the antitumoral property is known.

There, the physiological effect of ligninsulfonic acid and other lignin derivatives, in particular, the antiviral effect thereof against NDV (Newcastle Disease Virus) belonging to the paramyxovirus family and RSV (Rous Sarcoma Virus) belonging to the retrovirus family, to which AIDS virus also belongs, has been investigated leading to the completion of the invention.

SUMMARY OF THE INVENTION

The gist of the invention lies in a composition for anti-AIDS viral and other antiviral medicines having spent liquor from pulping and/or processed products as major constituents.

DETAILED DESCRIPTION OF THE INVENTION

First of all, the antiviral activity of sulfite spent liquor was determined to find that the activity is exhibited at about 1.5 mg/ml against NDV and at about 100 μg/ml against RSV. Next, the sulfite liquor was fractionated through ultrafilters (UK type) with fractional molecular weights of 10,000 and 1,000. The quantities of sugars, ashes and ligninsulfonic acid in each fraction were determined and the antiviral activity was tested to obtain results as shown in Table 1 below.

TABLE 1

|  | Sugars | Ashes | Lignin-sulfonic[*1] acid | Anti-NDV activity | Anti-RSV activity |
| --- | --- | --- | --- | --- | --- |
| Sulfite spent liquor[*2] | 24% | 38% | 37% | 1.5 mg/ml | 0.1 mg/ml |
| Fractional molecular weight Over 10,000 | 10 | 14 | 75 | 0.3 | 0.03 |
| Fractional molecular weight Over 1,000 and under 10,000 | 14 | 30 | 45 | 2.0 | 0.3 |
| Fractional molecular weight Under 1,000 | 33 | 55 | 12 | 7.5 | 2.0 |

[*1]Determined by glycol chitosan method
[*2]Residual ligin in pulp: 2.0%

As above, it has been found that the substance which exhibits the antiviral activity resides in ligninsulfonic acid and particularly the fraction which exhibits high activity is on the side of high molecular weight. However, this fact does not deny the existence of antivirus-active substances other than ligninsulfonic acid in sulfite spent liquor.

The methods of testing antiviral activity in the invention will be shown below.

In the test for anti-NDV activity, primary culture cells CEF (Chick Embryo Fibroblast) were proliferated on a plate with 96 holes and infected with NDV. Then, after 30 minutes, progressively diluted samples were added and, 24 hours later, the concentration to inhibit the cell fusion caused by virus was judged under microscope.

In the test for anti-RSV activity, following the proliferation of said CEF on a plate with 96 holes, this was infected with RSV. After 1 hour, progressively diluted samples were added and, 5 days later, the concentration to inhibit the transformation caused by virus was judged under microscope.

Next, the antiviral activity was determined for various lignin derivatives, too.

Results are shown in Table 2.

The methods of preparing samples in said table are as follows:

Sodium ligninsulfonate

Produced by treating calcium ligninsulfonate with caustic soda to exchange the base.

Calcium ligninsulfonate

Produced by cooking red pine with cooking liquor of calcium sulfite ($CaSO_3$).

Magnesium ligninsulfonate

Produced by cooking red pine with cooking liquor of magnesium sulfite ($MgSO_3$).

Kraft lignin

Produced by kraft pulping of red pine to field bleached kraft pulp (residual lignin in pulp: 2.0%). Composition of kraft spent liquor (inorganics 6.2%, sugars 2.8%, lignin 6.0%).

Dioxane ligin

Extracted from wood flour (spruce) treated with alcohol-benzene by heating for 2 hours at 175° C. in a mixed liquor of dioxane-water (1:1) according to the method of Sakakibara et al. The yield was about 45%.

Thioglycolic acid lignin

Prepared according to Brauns et al in a way that degreased wood flouor (birch) was added to a mixed liquor of thioglycolic acid with 2N hydrochloric acid to boil for 7 hours, the mass was then separated by filtration and, after washing with water and with ethanol, the residue was extracted with 2% sodium hydroxide. The lignin was recovered after precipitated with hydrochloric acid.

Sulfomethylated product of kraft lignin

Prepared in a way that $Na_2SO_3$ (10 to 20% based on kraft lignin) and then HCHO (equimols to $Na_2SO_3$) were added to slurry (about 25%) of kraft lignin to treat for 1 to 2 hours at 60° to 80° C. and, after treating further for 2 to 3 hours at 130° to 150° C., cooling and drying were made.

TABLE 2

| Sample | Anti-NDV activity | Anti-RSV activity |
| --- | --- | --- |
| Sodium ligninsulfonate | 0.3 mg/ml | 0.03 mg/ml |
| Calcium ligninsulfonate | 0.4 | 0.04 |
| Magnesium ligninsulfonate! | 0.2 | 0.03 |
| Kraft lignin | 1.2 | 0.1 |
| Dioxane lignin | 1.5 | 0.2 |
| Thioglycolic acid lignin1 | 0.8 | 0.1 |
| Sulfomethylated product of kraft lignin | 0.5 | 0.07 |

As above, the antiviral activity was recognized with all lignin derivatives listed in the table and thereamong ligninsulfonic acids proved to have potent antiviral effect. Besides, the lignin derivatives are not confined to those in the table and any known currently may be utilized.

In following, part of the invention will be exemplified based on the examples, but the invention is not confined to these.

EXAMPLE 1

Using dialyzing membrane, 100 ml of sulfite spent liquor shown in Table 1 was dialyzed for 4 days against tap water and for 3 days against deionized water in batch. The liquor having finished the dialysis was concentrated to about 30 ml with rotary evaporator and then freeze-dried to obtain about 3.5 g of fraction rich in ligninsulfonic acid. Both reducing sugar and ash in this fraction decreased to about one tenth compared with those of the original sulfite spent liquor. When determining the anti-NDV and anti-RSV activities, this fraction exhibited the effect at 0.5 mg/ml and 0.04 mg/ml, respectively.

EXAMPLE 2

After 100 ml of kraft spent liquor shown in Table 2 was adjusted to pH 3.0 to precipitate the portion of kraft lignin, this was centrifuged (10,000 rpm) to collect the precipitated fraction. Then, this was converted to powder by drying under reduced pressure to obtain about 4.0 g of fraction rich in kraft lignin. Suspending this into deionized water, 1N NaOH was added to completely dissolve and solution with a final concentration of 1% was prepared. When determining the anti-NDV and anti-RSV activities using said kraft lignin solution, the effect was seen at 0.8 mg/ml and 0.07 mg/ml, respectively, in terms of solids.

What is claimed is:

1. A method of treating a viral infection caused by NDV or RSV virus which comprises administering to a human being or animal under attack by said virus a lignosulfonate or kraft lignin in an amount effective for controlling said virus and for reducing the extent of infection caused by said virus.

2. The method of claim 1 wherein the lignosulfonate or kraft lignin is derived from spent liquor from pulping.

3. The method of claim 3 wherein the spent liquor is sulfite spent liquor or kraft spent liquor.

4. The method of claim 2 wherein the spent liquor is fractionated to yield a fraction of a molecular weight of not less than about 5,000.

5. The method of claim 1, wherein the lignosulfonate comprises at least one of dioxane lignin, thioglycolic acid lignin or sulfomethylated product of kraft lignin.

6. The method of claim 1, wherein the viral infection treated is caused by NDV virus.

7. The method of claim 1, wherein the viral infection treated is caused by RSV virus.

* * * * *